United States Patent
Matus Garcia et al.

(10) Patent No.: US 11,714,030 B2
(45) Date of Patent: Aug. 1, 2023

(54) MODULAR SYSTEM FOR UPSTREAM WASTEWATER SAMPLING

(71) Applicant: Biobot Analytics, Inc., Cambridge, MA (US)

(72) Inventors: Mariana G. Matus Garcia, Cambridge, MA (US); Newsha Ghaeli, Cambridge, MA (US); Nikhil B. Lal, Cambridge, MA (US); Noriko Endo, Cambridge, MA (US)

(*) Notice: Subject to any disclaimer, the term of this patent is extended or adjusted under 35 U.S.C. 154(b) by 910 days.

(21) Appl. No.: 16/528,465

(22) Filed: Jul. 31, 2019

(65) Prior Publication Data
US 2020/0072709 A1    Mar. 5, 2020

Related U.S. Application Data (60) Provisional application No. 62/712,959, filed on Jul. 31, 2018.

(51) Int. Cl.
| | | |
|---|---|---|
| G01N 1/20 | (2006.01) | |
| G01N 1/14 | (2006.01) | |
| G01N 1/40 | (2006.01) | |
| G01N 33/18 | (2006.01) | |
| G01N 1/10 | (2006.01) | |

(52) U.S. Cl.
CPC .............. G01N 1/20 (2013.01); G01N 1/14 (2013.01); G01N 1/405 (2013.01); G01N 1/4077 (2013.01); G01N 33/1826 (2013.01); G01N 2001/1043 (2013.01); G01N 2001/1427 (2013.01); G01N 2001/4088 (2013.01)

(58) Field of Classification Search
CPC .......... G01N 1/14; G01N 1/20; G01N 1/2035; G01N 1/405; G01N 1/4077; G01N 2001/1043; G01N 2001/1427; G01N 2001/2064; G01N 2001/2071; G01N 2001/4088; G01N 33/1826
USPC ........................................... 73/863.23
See application file for complete search history.

(56) References Cited

U.S. PATENT DOCUMENTS 9,638,828 B2 * 5/2017 Levien ................. B64C 39/024
9,656,894 B2 * 5/2017 Snydmiller ............ C10G 33/04
(Continued)

FOREIGN PATENT DOCUMENTS

| CN | 1290859 A | * | 4/2001 |
| CN | 214373606 U | * | 10/2021 |
| JP | 2001165927 A | * | 6/2001 |

(Continued)

*Primary Examiner* — Helen C Kwok
*Assistant Examiner* — Nashmiya S Fayyaz
(74) *Attorney, Agent, or Firm* — Dinsmore and Shohl (57) ABSTRACT

A wastewater sampling system including: an inlet tube; an outlet port; a high-flow circuit fluidly coupling the inlet tube to the outlet port; a first pump, along the high-flow circuit, configured to pump wastewater through the high flow circuit; a sampling circuit, fluidly coupled to the high-flow circuit via a junction, comprising a solid waste filter fluidly coupled to the junction and a solid-phase extraction cartridge fluidly coupled to an outlet of the solid waste filter; a second pump along the sampling circuit; a controller configured to, during a sampling cycle at a first time, activate the first pump; at a second time, activate the second pump; and at a third time succeeding the second time by a sampling duration, deactivate the second pump.

1 Claim, 5 Drawing Sheets

(56) References Cited

U.S. PATENT DOCUMENTS

2009/0103086 A1* 4/2009 Stark .................... G01N 1/4077
356/326
2020/0385296 A1* 12/2020 Garcia ............... G01N 33/1866

FOREIGN PATENT DOCUMENTS

| WO | WO-2016146970 A1 * | 9/2016 | ............. G01N 33/18 |
| WO | WO-2019215000 A1 * | 11/2019 | ............. F04D 13/06 |

* cited by examiner

MODULAR SYSTEM FOR UPSTREAM WASTEWATER SAMPLING

CROSS-REFERENCE TO RELATED APPLICATIONS

This Application claims the benefit of U.S. Provisional Application No. 62/712,959, filed on 31 Jul. 2018, which is incorporated in its entirety by this reference.

TECHNICAL FIELD

This invention relates generally to the field of wastewater sampling and more specifically to a new and useful system for obtaining wastewater samples upstream from a water treatment facility.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

Figure 1A:
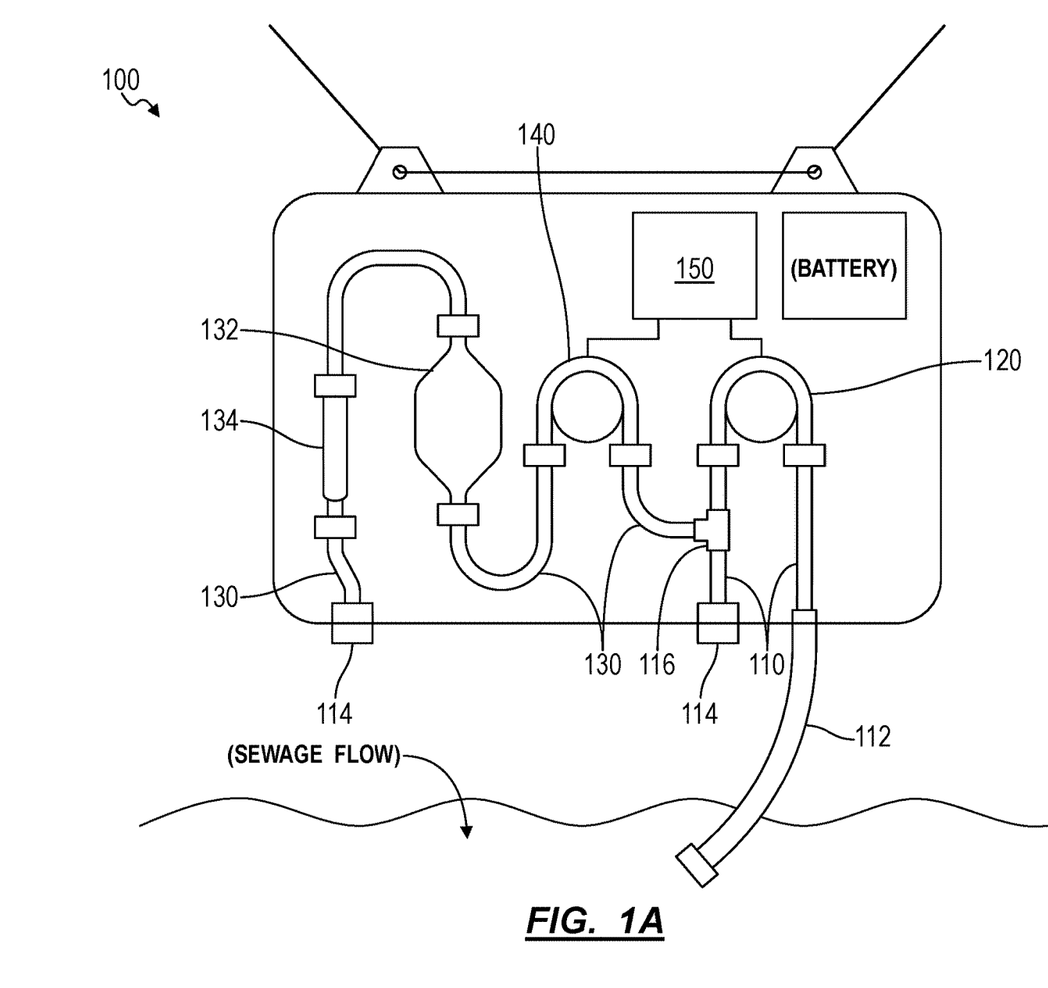
FIGS. 1A and 1B are schematic representations of a system.

As shown in FIG. 1A, a wastewater sampling system 100 can include: an inlet tube 112 configured to extend into a sewage flow; an outlet port 114; a high-flow circuit 110 fluidly coupling the inlet tube to the outlet port 114; and a first pump 120 positioned along the high-flow circuit 110 and configured to pump wastewater from the sewage flow, through the inlet tube 112, and out of the outlet port 114. The wastewater sampling system 100 also includes a sampling circuit 130 fluidly coupled to the high-flow circuit 110 via a junction 116 and including: a solid waste filter 132 fluidly coupled to the junction 116; and a solid-phase extraction cartridge 134 fluidly coupled to an outlet of the solid waste filter 132. The wastewater sampling system 100 additionally includes a second pump 140 positioned along the sampling circuit 130. The wastewater sampling system 100 further includes a controller 150 configured to, during a sampling cycle: at a first time, activate the first pump 120 to initiate flow of wastewater from the sewage flow through the high-flow circuit 110; at a second time, activate the second pump 140 to divert wastewater from the high-flow circuit 110 into the sampling circuit 130 via the junction 116; and, at a third time succeeding the second time by a sampling duration, deactivate the second pump 140.

Figure 1B:
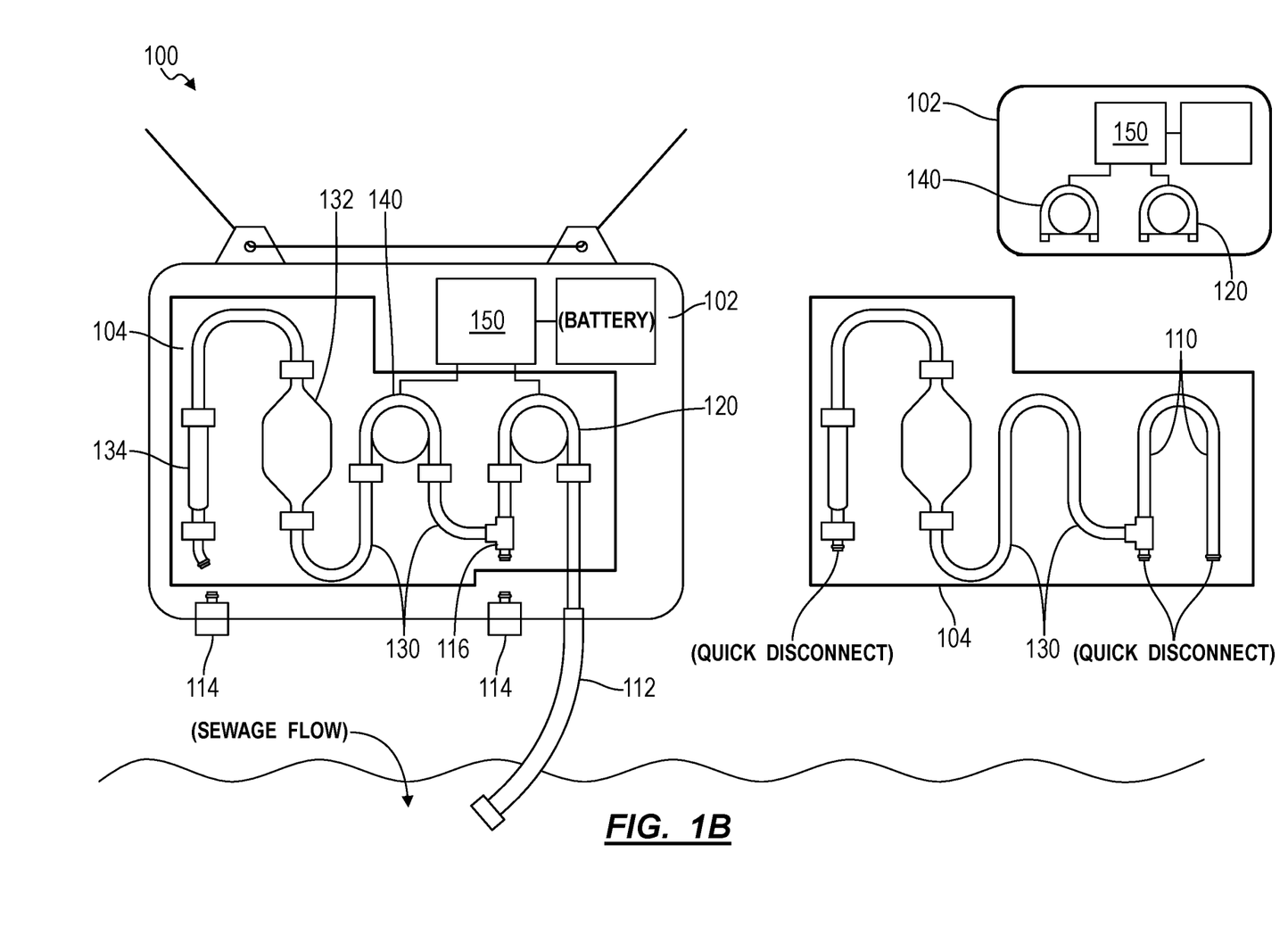

As shown in FIG. 1B, one variation of the wastewater sampling system can include a sampling assembly 102 and a replaceable filter kit 104. The sampling assembly 102 includes: an inlet tube 112 configured to extend into a sewage flow; a first peristaltic pump; a first outlet port 114; a second peristaltic pump; a second outlet port 114; and a controller 150. The replaceable filter kit 104 includes: a high-flow circuit 110 configured to connect with the inlet tube 112 and the first outlet port 114 and engage with the first peristaltic pump in the sampling assembly 102; and a sampling circuit 130. The sampling circuit 130 is: fluidly coupled to the high-flow circuit 110 via a junction 116; configured to engage with the second peristaltic pump in the sampling assembly 102 and connect with the second outlet port 114 in the sampling assembly 102; and comprising a solid waste filter 132 fluidly coupled to the junction 116 and a solid-phase extraction cartridge 134 fluidly coupled to an outlet of the solid waste filter 132. Additionally, in this variation the controller 150 is configured to, during a sampling cycle and while the replaceable filter kit 104 is engaged with the sampling assembly 102: at a first time, activate the first peristaltic pump to initiate sewage flow through the high-flow circuit 110; at a second time succeeding the first time, activate the second peristaltic pump to divert sewage flow from the high-flow circuit 110 into the sampling circuit 130 via the junction 116; and at a third time succeeding the second time by a sampling duration, deactivate the second peristaltic pump.

Figure 2:
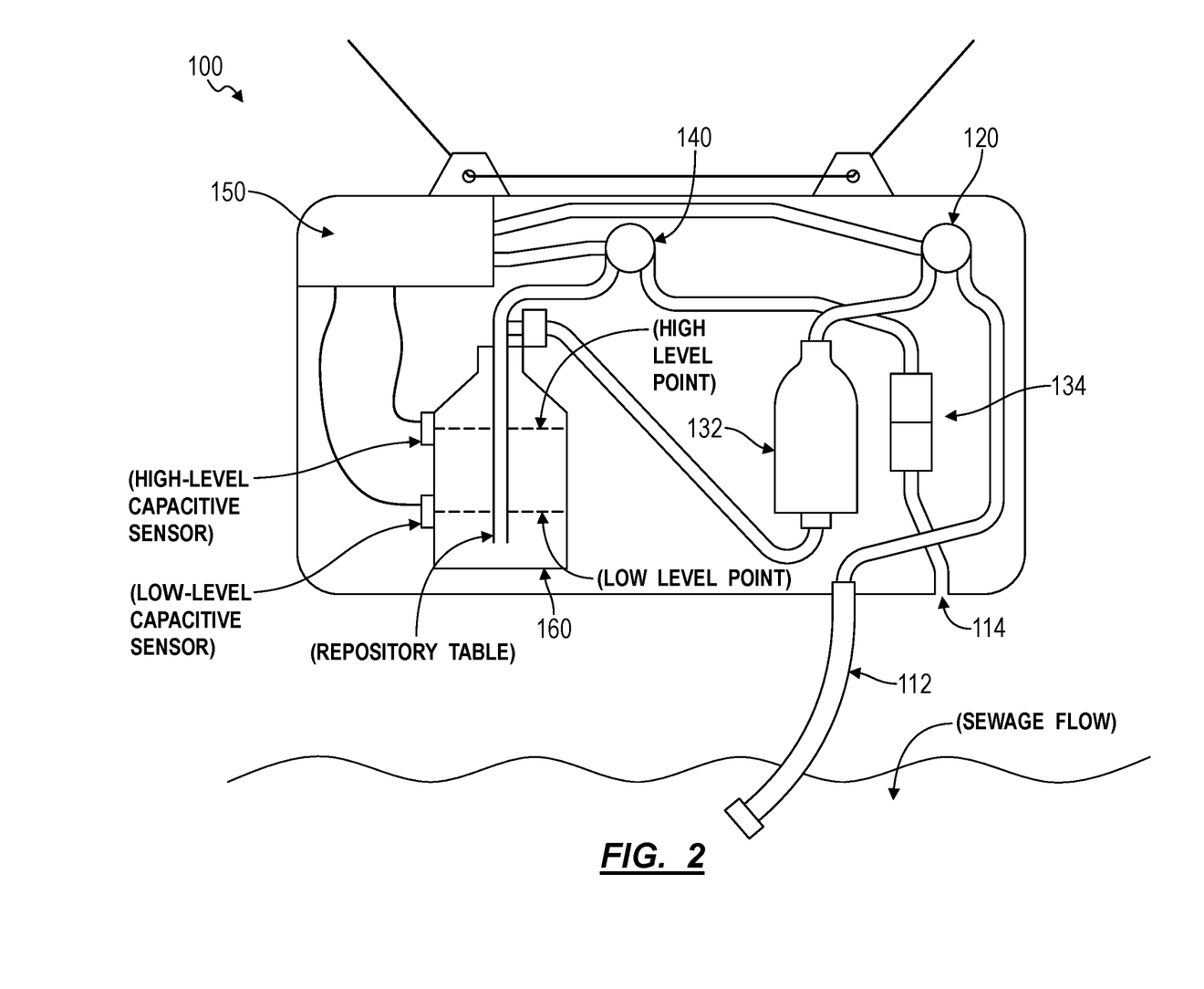
FIG. 2 is a schematic representation of a variation of the system.

As shown in FIG. 2, another variation of the wastewater sampling system includes an inlet tube 112 extending into a sewage flow; a first pump 120 configured to pump wastewater from the sewage flow into the wastewater sampling system; a solid waste filter 132 fluidly coupled to the inlet tube 112; a solid-phase extraction cartridge 134 fluidly coupled to an outlet of the solid waste filter 132; and a second pump 140 configured to pump volumes of wastewater through the solid waste filter 132 and the solid-phase extraction cartridge 134. This variation also includes a controller 150 configured to periodically execute a series of sampling cycles over a sampling period; and for each sampling cycle in the series of sampling cycles, access a target flow rate of the second pump 140 proportional to an approximate flow rate of the sewage flow during the sampling cycle. In this variation, the controller 150 is further configured to, during each sampling cycle in the series of sampling cycles: at a first time, activate the first pump 120 to initiate sewage flow into the wastewater sampling system; at a second time succeeding the first time, activate the second pump 140 to pass wastewater through the solid waste filter 132 and the solid-phase extraction cartridge 134 at the target flow rate; and at a third time succeeding the second time by a sampling duration, deactivate the second pump 140.

2. Applications

Generally, the wastewater sampling system 100 (hereinafter "system 100") is an upstream wastewater sampling device configured to: be suspended above a sewage flow proximal to a sewage access point (e.g. a manhole); periodically sample wastewater from the sewage flow in a precise dosage; filter solid waste from a wastewater sample; and draw the wastewater sample through a solid-phase extraction (hereinafter "SPE") cartridge to extract dissolved drug metabolites in the wastewater sample. The system 100 also includes easily replaceable and serviceable components, which reduce the need for onsite servicing, thereby limiting deployment and redeployment costs while also ensuring consistent sampling. The system 100 provides government organizations or other interested parties the ability to sample wastewater upstream (in terms of the sewage flow in the sewer network) from a wastewater treatment facility. By being positioned upstream, the system 100 can be deployed closer to sources of residential wastewater, which may contain drug metabolites, drug components, other indicators of drug use, or any other chemical of interest from a particular residential area. These drug metabolites and other chemicals of interest may be consumed by bacteria in wastewater or otherwise decay in the sewage flow before arriving at a water treatment facility. Therefore, the system 100 is configured to collect a stable sample of wastewater containing detectable amounts of drug metabolites and to separate these drug metabolites from biological solid waste that may otherwise consume or contaminate these drug metabolites, thereby enabling accurate, localized monitoring of drug consumption within a geographic region. Furthermore, by streamlining deployment and redeployment to limit per unit cost and deployment time, many instances of the system 100 can be distributed within a geographical region (e.g. an urban area or city) to obtain high-resolution, localized, repeatable drug consumption data for a population within this geographic region.

In addition to an SPE cartridge 134 for extracting drug metabolites and other chemicals dissolved in the wastewater, the system 100 also includes a solid waste filter 132, which traps a sample of the microbiome present in the wastewater. Therefore, in one implementation, the system 100 can collect chemical samples in the SPE cartridge 134 for later analysis using mass spectrometry, as well as solid waste samples in the solid waste filter 132 for later analysis using DNA sequencing, such as 16S rDNA sequencing, to identify bacterial species in the solid waste sample. Additionally or alternatively, the system 100 can include a fluid repository 160 which can preserve a wastewater sample in a stable environment (i.e. without bacteria in the sample) for later analysis or as a "B sample" for verification of the original sample.

In one application of the system 100, multiple instances of the system 100 can be strategically deployed throughout a sewer network, such that each wastewater sampling device can sample wastewater from a primarily residential area with demographics representative of a larger area of a city. Thus, by analyzing sewer network data, land use data, and demographic data to deploy the system 100, the system 100 can enable estimation of illicit drug usage or otherwise monitor the public health of a population of a geographic region.

Once deployed at a sewer access point, the system 100 can periodically initiate a sampling period, during which the system 100 can execute sampling cycles to obtain wastewater samples from the sewage flow. The system 100 can utilize a sampling period of any duration such as a twenty-four-hour period (i.e. daily sampling period), weekly sampling period, or monthly period depending on the implementation. In some implementations, the system 100 can also initiate the sampling period such that the end of the sampling period coincides with a scheduled pick-up or exchange of the SPE cartridge 134, solid waste filter 132, and/or the fluid repository 160, such that the sample may be analyzed shortly after it has been collected by the system 100, thereby reducing degradation of the sample before analysis.

The system 100 can also be configured to be serviced or replaced entirely after the completion of a sampling period. Alternatively, the system 100 can include multiple SPE filters, which would enable additional sampling periods. In one application, the system 100 defines a modular structure, which includes many of the replaceable components of the system 100, such as the solid waste filter 132, the fluid repository 160, and the SPE cartridge 134, which can be easily replaced or exchanged. In another implementation, the system can include a sampling assembly 102, which includes the controller 150, pumps, the external casing, and other permanent and/or reusable components of the system 100, and a replaceable filter kit 104, which can include all single use components of the system, such as the solid waste filter 132, the SPE cartridge 134, connective tubing, and/or the fluid repository 160. Therefore, a user servicing or collecting samples from the system 100 can remove all replaceable components as a single unit.

The system 100 includes a controller 150 arranged within the external casing of the system 100 that initiates sample cycles and executes other functions. Alternatively, the system can interface with an external controller 150 to trigger particular functions of the system 100.

One variation of the system 100 includes an inlet tube 112, a first pump 120, a fluid repository 160, a second pump 140, a solid waste filter 132, and an SPE cartridge 134. In this variation, the system, via the controller 150, initiates intake of a wastewater sample from the sewage flow through the inlet tube 112 by activating the first pump 120. The first pump 120 draws the wastewater through the solid waste filter 132, which removes solid waste and bacteria from the wastewater. The system 100 continues to draw wastewater from the inlet tube 112 via the controller 150 until a sampling volume has accumulated in the fluid repository 160. Once the sample volume of wastewater has accumulated, the system 100 deactivates the first pump 120, thereby stopping the flow of wastewater through the solid waste filter 132 and into the fluid repository 160. The system then activates a second pump 140 to draw a sampling volume from the fluid repository 160 and through the SPE cartridge 134, thereby accumulating chemical samples within the SPE cartridge 134 for later analysis.

In another variation, the system 100 can include two fluid circuits, a high flow circuit and a sampling circuit 130, along with the inlet tube 112, the first pump 120, the second pump 140, the solid waste filter 132, and the SPE cartridge 134. In this variation, the high-flow circuit 110 connects the inlet tube 112 to an outlet port 114, while the sampling circuit 130 is fluidly coupled to the high-flow circuit 110 via a junction 116 in the high-flow circuit 110. The sampling circuit 130 connects to the junction 116 in the high-flow circuit 110 and includes the solid waste filter 132 and the SPE cartridge 134. In this variation, during a sampling cycle, the system 100 can activate the first pump 120, via the controller 150 to draw wastewater water up from the sewage flow, into the system 100 and back out of the outlet port 114. While the first pump 120 is activated and wastewater is flowing through the high-flow circuit 110, the system 100 activates the second pump 140 to divert water from the high-flow circuit 110 into the sampling circuit 130 thereby collecting samples in both the solid waste filter 132 and SPE cartridge 134. In this variation, the second pump 140 is configured to divert precise volumes of wastewater from the high-flow circuit 110 in order to produce accurate drug metabolite samples in the SPE cartridge 134.

In some implementations, the controller 150 is configured to perform additional functions such as: illuminating an LED indicator; timing the intake of the sampling volume; reading capacitive sensors arranged proximal to the fluid repository 160 to determine fluid levels; and/or reading values from a flowmeter. The system 100 can also include a controller 150 configured to adjust the timing of the sampling period, the sampling interval, and the sampling cycle. Furthermore, the system 100 can include a controller configured to adjust the flowrate of either the first pump 120 or the second pump 140 of the system 100.

The system 100 is described herein with reference to the collection of wastewater samples for drug metabolite detection and drug consumption analysis. However, the system 100 can be deployed to collect waterborne samples for any other application, such as public health monitoring.

3. Deployment

The system 100, can be deployed proximal to or above a waste water flow in a sewer network. In some implementations the system 100 can be deployed proximal to a sewer access point such as a manhole cover or manhole. The placement of the system 100 proximal to a sewer access point allows for easy access to the system for servicing and also allows for some standardization in the deployment of the system 100. Depending on the application of the system 100, the system can be deployed in a predominantly residential area (e.g. for monitoring illicit drug consumption), or a predominantly industrial area (e.g. for monitoring pollution levels in the wastewater). Ideally, the system 100 is deployed at a location in the sewer network that typically experiences greater than a minimum level of sewage flow such that the system 100 can extract a representative sample from the sewage flow. For example, if the minimum flow level at a specific location in the sewer network results in a water level too low for the system 100 to retrieve a sample, the specific location may not be a suitable location for deployment of the system 100. Likewise, the system 100 is deployed at a location in a sewer network that experiences maximum flow levels that are not typically capable of displacing or otherwise damaging the system 100.

The system 100 can be configured to be deployed quickly with tools available to public works employees or other government workers with access to the sewer network. Any organization deploying the system 100 can analyze sewer network, land use, and demographic data to determine how to best deploy the system 100 to accomplish the specific wastewater sampling task that will be performed. As such, the deployment of the system 100 can be performed in any other way.

4. Suspension and External Casing

The system 100 includes an external casing that houses many of the other components of the system 100. Generally, the system 100 includes an external casing that defines inlet and outlet port 114s for sampling and removing water from the system 100, a means of mounting the system 100 proximal to the sewer access point, and any openings for communication via LED indicators (e.g. visual communication with anyone tasked with servicing the system 100) or antennas for wireless communication with a remote device. The system 100 also includes an external casing that is waterproof to prevent ingress of water into the system and therefore the potential for corrosion of the internal (e.g. electrical) components of the system 100 or for contamination of the samples collected by the system 100. Additionally, the system 100 can include an external casing that is sufficiently robust to resist impact from dropping the system or other physical impact associated with the deployment of the system 100. In one implementation, the system 100 includes an external casing made of a hard and durable plastic to prevent corrosion and provide impact resistance and durability.

In one implementation, the system 100 includes an external casing configured to be suspended from the sides of a manhole over a sewage flow. For example, the system 100 can include an external casing with eyelets or other connection points or loops through which a cable can be attached or otherwise pass through the external casing of the system 100. The cable can then be attached to mounting brackets screwed to either side of the manhole. Thus, the system 100 can hang via a cable attached to two brackets on either side of the manhole, such that the system 100 is suspended above a sewage flow. However, the system 100 can be suspended or mounted to the walls or pipes of the sewer network above the sewage flow via the external casing in any other way.

Therefore, the system 100 can include an external casing suspended above a sewage flow at a sewage access point and that houses: a high-flow circuit 110; a first pump 120; a sampling circuit 130; a second pump 140; and a controller 150. Additionally, the system 100 can include an inlet tube 112 coupled to the external casing and traversing the external casing to extend into the sewage flow; and an outlet port 114 coupled to the external casing and traversing the external casing.

Additionally, the external casing can function to locate any of the externally contained components relative to each other such that each component of the system 100 can be fluidly coupled, as further described below. Furthermore, in implementations including a replaceable filter kit 104, the external casing can include clips, buckles, snaps or any other type of mechanical attachment configured to transiently couple with the replaceable filter kit 104 and locate the replaceable filter kit 104 appropriately within the sampling assembly 102, as further described below.

5. Inlet Tube

The system 100 includes an inlet tube 112 that is coupled to the external casing (and traverses a shell of the external casing) and extends below the surface of the sewage flow. Generally, the system 100 includes an inlet tube 112 that can intake a sample volume of wastewater from the sewage flow without being occluded or dislodged from the system 100 by debris in the sewage flow. The system 100 can also include an inlet tube 112 that is flexible and chemically inert, such as silicon rubber, such that the inlet tube 112 can bend or otherwise move with the sewage flow to provide more consistent wastewater samples for the system 100.

In one implementation, the system 100 includes an inlet tube 112 transiently coupled to an inlet port on the external casing while being fluidly coupled to the internal tubing of the system. For example, the inlet tube 112 can be attached via a latching mechanism or via a magnetic attachment system to minimize externally facing surfaces to which debris in the wastewater may attach. By including a transiently attached inlet tube 112, the system 100 can be more easily and/or more sanitarily serviced, since the only component that comes into external direct contact with the sewage flow can be easily removed and discarded while handling the system 100 for extraction of samples or general servicing. Additionally, the system 100 including a transiently coupled inlet tube 112 can be modified with inlet tubes 112 of varying lengths, depending on the height above the sewage flow at which the system 100 is suspended and/or the average or minimum depth of the sewage flow.

In one implementation, the system 100 can include an inlet tube 112 fitted with a mesh or grate over the submerged end of the inlet tube 112. The mesh or grate can include millimeter scale holes in order to preventing large debris or particulates from entering the system 100 during intake of a wastewater sample.

In one implementation, the system 100 can include a flowmeter that is weighted or buoyed to position the submerged opening of the inlet tube 112 more precisely in the sewage flow. For example, the inlet tube 112 can be coupled to a weight at the submerged end in order to further submerge the inlet into the sewage flow. Alternatively, a buoy or a buoyant object can also be positioned at the submerged end of the inlet tube 112 allowing the submerged end to float closer to the surface of the sewage flow. Furthermore, the system 100 can include an adjustable buoyancy system that can increase or decrease buoyancy of the inlet tube 112 to consistently place the inlet tube 112 within the sewage flow. Any weight, buoy, or adjustable buoyancy system can be mechanically coupled to the submerged end of the inlet tube 112 such that there is a smooth interface between the weight, buoy, or adjustable buoyancy system, thereby preventing debris from collecting on irregular interfaces between the inlet tube 112 and any weight, buoy, or buoyancy system.

In one implementation, the system 100 can include a flowmeter coupled to the inlet tube 112 configured to estimating the flow rate of the sewage flow; the system 100 can then increase or decrease the sampling rate depending on the flow rate of the sewage flow. Furthermore, the system 100 can include a flowmeter that is detachable from the inlet tube 112, such that the inlet tubes 112 can be discarded independent of the flowmeter.

However, the system 100 can include an inlet tube 112 that extends below the surface of the sewage flow in any other way.

6. Fluid Repository Variation

A shown in FIG. 2, in one variation of the system 100, the system 100 includes a fluid repository 160 for dosing a particular volume of wastewater for a particular wastewater sample. In this variation, the fluid repository 160 is fluidly coupled between the outlet of the first pump 120 and the inlet of the second pump 140 and functions to contain a stable sample of wastewater (e.g., without significant bacteria populations before the system 100 pumps the measured volume of wastewater through the SPE cartridge 134. This variation is described in more detail below.

6.1 Solid Waste Filter

In the variation of the system 100 including the fluid repository 160, the system 100 includes a solid waste filter 132 configured to filter solid biological waste from the wastewater sample as it flows into the system 100 and before the wastewater sample is deposited in the fluid repository 160. Generally, the solid waste filter 132 removes bacteria and other large debris from the wastewater sample in order to prevent bacteria in the wastewater sample from changing the chemical composition of the wastewater sample as it sits stagnant in the fluid repository 160. An inlet of the solid waste filter 132 is fluidly coupled to the inlet tube 112 via internal tubing, and the solid waste filter 132 receives the wastewater sample before other components of the system 100.

In one implementation, the system 100 includes a solid waste filter 132 with a pore size of less than 0.5 microns (i.e. sufficiently small to remove bacterial from the wastewater sample). Additionally, the system 100 can include a solid waste filter 132 that has a chemically inert filtering medium, so as not to affect the chemistry of the wastewater sample.

In one implementation, the system 100 includes a solid waste filter 132 that is replaceable and configured to be disconnected from the surrounding internal tubing by a user interfacing with the system 100. In one implementation, the filtering medium can be removed from the housing of the solid waste filter 132 for testing, cleaning and sterilization, or replacement. Additionally, the contents of the solid waste filter 132 can be tested by users of the system 100. Therefore, the system 100 can include a solid waste filter 132 that is compatible with 16S rDNA sequencing, micro-biological culture, or any other bacterial or viral profiling test. In one implementation, the system 100 can include multiple successive solid waste filters 132 of increasingly small pore size to better separate solid waste from free floating bacteria and/or viruses. The system 100 can include a viral filter as part of a secondary solid waste filter 132, wherein the viral filter has a pore size of less than 0.1 microns. Thus, the system 100 can include a pore size configured to capture bacteria and/or viruses from wastewater.

However, the system 100 can remove bacteria and other solid waste from the sample in any other way.

6.2 Fluid Repository

In the variation shown in FIG. 2, the system 100 includes a fluid repository 160 for dosing and storing a sampling volume of wastewater between filtering steps or for later secondary filtering and analysis. Generally, the fluid repository 160 is a fluid container including a plastic, or otherwise chemically inert rigid shell (e.g. a polycarbonate shell), which defines precise volumes of its fluid contents at various fluid levels within the fluid repository 160, when the system 100 is in its sampling orientation (e.g. when the system 100 is suspended as intended above a sewage flow). More specifically, the system 100 can include: a fluid repository 160 fluidly coupled to an outlet of the solid waste filter 132 and the inlet of the solid-phase extraction cartridge 134, wherein a first pump is configured to pump wastewater from the sewage flow into the fluid repository 160 via the inlet tube 112 and wherein a second pump 140 is configured to pump wastewater from the fluid repository 160 through the solid waste filter 132 and the solid-phase extraction cartridge 134.

The system 100 can include a fluid repository 160 configured in a shape resistant to residual wastewater adhering to the sides of the fluid repository 160 in the form of droplets (e.g. a cone shape, or a bottle shape with vertical walls), such that the volume of wastewater contained within the fluid repository 160 can be measured accurately via the fluid level in the fluid repository 160. Additionally or alternatively, the fluid repository 160 can be internally coated with or entirely composed of a chemically inert hydrophobic material such that wastewater does not accumulate on the walls of the fluid repository 160.

In one implementation, the system 100 includes a fluid repository 160 that defines two fluid volumes, a first volume at a low-level point on the side of the fluid repository 160 and a second volume at a high-level point on the side of the fluid repository 160. Additionally, the system 100 includes a fluid repository 160 defining the first volume and second volume such that the second volume is greater than the first volume by a sampling volume. Furthermore, the system 100 can include a fluid repository 160 defining a low-level point indicating a first volume indicating a sampling volume. For example, the low-level point of the fluid repository 160 can indicate a volume of 500 milliliters of wastewater contained in the fluid repository 160 and the high-level point in the fluid repository 160 can indicate a volume of 1000 milliliters of wastewater contained within the fluid repository 160, thereby indicating a sampling volume of 500 milliliters. In one implementation, the system 100 defines the volume below the low-level point as a secondary sample volume. The secondary sample volume can function, similar to a running average, as a preserved sample of the wastewater that has been filtered through the SPE cartridge 134 over a sampling period. The system 100 can include a fluid repository 160 that is capable of preserving the secondary sample in the fluid repository 160 even after the fluid repository 160 has been removed from the system and stored for later analysis. If the SPE cartridge 134 is lost or is otherwise compromised, users of the system 100 can retrieve a corresponding secondary sample from storage and run additional tests to recover, confirm, or validate the tests conducted on the corresponding SPE cartridge 134.

Aiding in the function of preventing wastewater accumulation on the walls of the fluid repository 160, the system 100 can additionally include one or more repository tubes, wherein each repository tube is fluidly coupled to the other components in the system 100, such as the solid waste filter 132, the pumps, and/or the SPE cartridge 134. In an implementation in which the system 100 includes a single repository tube, the repository tube can extend from the top of the fluid repository 160 (when the fluid repository 160 is in its sampling orientation) and define an opening near the bottom of the fluid repository 160 or below the low-level point of the fluid repository 160, such that any wastewater exiting the repository tube flows into the bottom of the fluid repository 160 without splashing against the internal walls of the fluid repository 160. In the implementation in which the system 100 includes a single repository tube, the repository tube functions to deposit a wastewater sample in the fluid repository 160 after solid waste filtering and remove a sampling volume from the fluid repository 160 for filtering by the SPE cartridge 134. In this case, the system 100 can include a three-way tube junction 116 or two-way diverter valve fluidly coupled to the repository tube external to the fluid repository 160, such that fluid can alternately pass into the fluid repository 160 from a solid waste filter 132 via the repository tube or pass out of the fluid repository 160 to an SPE cartridge 134 via the same repository tube. For example, a first interface of the three-way tube junction 116 or two-way diverter valve can be coupled to an outlet of the solid waste filter 132, a second interface can be fluidly coupled to the repository tube, and the third interface can be fluidly coupled to an inlet of the SPE cartridge 134.

Alternatively, in an implementation in which the system 100 includes multiple repository tubes, an inlet repository tube can extend from outside the fluid repository 160 to define an opening below the low-level point of the fluid repository 160, while an outlet repository tube can extend from outside the fluid repository 160 to define an opening at the low-level point (such that the outlet repository tube can empty the fluid repository 160 only to the low-level point). In this implementation in which the system 100 includes an inlet and outlet repository tube, the inlet tube 112 is fluidly coupled to the outlet of the solid waste filter 132 while the outlet repository tube is fluidly coupled to the inlet of the SPE cartridge 134.

In addition to one or more repository tubes, the system 100 can also include a fluid repository 160 fitted with a pressure release valve to relieve air pressure within the fluid repository 160, which may have accumulated after pumping a wastewater sample into the fluid repository 160. The pressure release valve of the system 100 is configured to release air upon exposure to a threshold air pressure gradient between the internal pressure of the fluid repository 160 and the ambient pressure within the system 100. The pressure release valve can be positioned above the high-level point of the fluid repository 160, such that the pressure release valve does not release wastewater contained within the fluid repository 160 into the system 100. In one implementation, the system 100 includes a pressure release valve that is ported to the outside of the external casing such that any gas expelled from the wastewater sample does not accumulate within the external casing of the system 100.

However, the system 100 can include a fluid repository 160 capable of storing and accurately dosing samples of wastewater in any other configuration.

6.2.1 Low-Level and High-Level Capacitive Sensors

The system 100 can include low-level and high-level capacitive sensors arranged external to the fluid repository 160 at the low-level point and the high-level point respectively. Generally, the low-level capacitive sensor functions to precisely measure or detect the absence of wastewater at the low-level point in the fluid repository 160 via a change in a capacitance of the low-level capacitive sensor. Meanwhile, the high-level capacitive sensor functions to precisely measure or detect the presence of wastewater at the high-level point in the fluid repository 160 via a change in a capacitance of the low-level capacitive sensor. More broadly, the system 100 includes the capacitive sensors to detect the presence or absence of fluid in the fluid repository 160, for the purpose of dosing the sampling volume of wastewater, without coming into contact with the wastewater. By including sensors that do not come into direct contact with the wastewater sample, the system 100 avoids corrosion of the sensor or potential requirement for the sensor to be made chemically inert. Instead the system 100 includes a sensor that can detect the presence or absence of wastewater inside the fluid repository 160 without being in direct contact with the wastewater sample.

In one implementation, the system 100 includes capacitive sensors coupled to the external casing proximal to an attachment point for a removable fluid repository 160, such that when a removable fluid repository 160 is inserted into the system via the attachment point the low-level point and the high-level point of the fluid repository 160 align with the low-level capacitive sensor and the high-level capacitive sensor respectively. Alternatively, the system 100 can include a fluid repository 160 with attachment points, such as snaps or clips, at the low-level point and the high-level point of the fluid repository 160, configured to attach to the low-level capacitive sensor and the high-level capacitive sensor respectively. The system 100 can be calibrated using to the controller 150 to determine whether the capacitive sensors are providing the correct signals to the controller 150 in response to the wastewater level in the fluid repository 160.

However, the system 100 can include any type of sensor to detect the fluid level within the fluid repository 160 without coming into contact with a wastewater sample in the fluid repository 160.

6.3 Solid-Phase Extraction Cartridge

The system 100 includes an SPE cartridge 134 configured to extract dissolved drug metabolites from water. Generally, the SPE cartridge 134 provides a means for extracting drug metabolites, other drug associated chemicals, or any other chemicals present in the wastewater sample for later analysis via mass spectrometry of the extracted chemicals from the SPE cartridge 134, upon removal of the SPE cartridge 134 from the system 100. Thus, the system 100 includes a removable and replicable SPE cartridge 134. The system 100 includes the SPE cartridge 134 with an inlet fluidly coupled to the outlet of the fluid repository 160 and an outlet fluidly coupled to the outlet port 114 of the external casing and the overall system 100. Therefore, after pumping the wastewater through the SPE cartridge 134, the system can route the wastewater sample through an outlet port 114 of the external casing to discard the sample.

In one implementation, the system 100 includes an SPE cartridge 134 with a stationary phase having analytes configured to bind with target functional groups of particular drug metabolites or other target chemicals that may be present in the wastewater sample. Therefore, the system can include a SPE cartridge 134 configured to extract drug metabolites from wastewater while sewage flows through the SPE cartridge 134. However, the system 100 can extract drug metabolites or other target chemicals from the wastewater sample in any other way.

In one implementation, the system 100 includes a set of multiple SPE cartridge 134s and each SPE cartridge 134 is included in its own sampling circuit 130 in the system 100. For example, each SPE cartridge 134 in the set can be individually fluidly coupled to the fluid repository 160 (e.g. via multiple tube junction 116s or diverter valves) and to the outlet port 114 furthermore each SPE cartridge 134 can include an associated pump (further described below) to move wastewater samples through each SPE cartridge 134. Alternatively, the system 100 can include a single pump coupled to a diverter valve to selectively pump water through each of the set of SPE cartridge 134s. More specifically, the system 100 can include: a diverter valve fluidly coupled to the outlet of the fluid repository 160 and defining a set of outlets; and a set of SPE cartridge 134s, each SPE cartridge 134 in the set of SPE cartridge 134s fluidly coupled to an outlet in the set of outlets defined by the diverter valve; and a controller 150 configured to: during a first sampling cycle, activate the first pump 120 to direct wastewater flow to a first SPE cartridge 134; and, during a second sampling cycle, actuate the diverter valve to direct flow of wastewater to a second solid-phase extraction cartridge 134 in the set of solid-phase extraction cartridges 134. Thus, the system 100 can be capable of performing multiple sampling periods before being serviced or replaced.

6.4 Pumps, Tubes, and Valves

The system 100 can include a first pump 120 and a second pump 140 for moving wastewater through various components of the system 100 via a series of tubes and valves. Generally, in the variation of the system 100 including a fluid repository 160, the system can include two pumps: the first pump 120 pumps the wastewater sample from the sewage flow, through the inlet tube 112, through the solid waste filter 132, and into the fluid repository 160; the second pump 140 pumps the wastewater sample from the fluid repository 160, through the SPE cartridge 134, and out of the outlet port 114 in the external casing. As such, the system 100 can include a first pump 120 that is fluidly coupled, at an inlet of the first pump 120, to the inlet tube 112 and fluidly coupled, at an outlet of the first pump 120 to the inlet of the solid waste filter 132. Alternatively, the system 100 can include a first pump 120 fluidly coupled, at an inlet of the first pump 120, to the outlet of the solid waste filter 132 and fluidly coupled, at an outlet of the first pump 120 to the fluid repository 160. Additionally, the system 100 can include a second pump 140 that is fluidly coupled, at an inlet of the second pump 140, to an outlet of the fluid repository 160 and fluidly coupled, at an outlet of the second pump 140 to the inlet of the SPE cartridge 134. Alternatively, the system 100 can include a second pump 140 fluidly coupled, at an inlet of the second pump 140, to an outlet of the SPE cartridge 134 and fluidly coupled, at an outlet of the second pump 140 to the outlet port 114.

As discussed with reference to the SPE cartridge 134, the system 100 can include additional pumps for each additional SPE cartridge 134 included in the system 100, such that each pump can individually pump wastewater samples through a fluid path corresponding to an SPE cartridge 134.

The system 100 can include various types of pumps such as peristaltic pumps, diaphragm pumps, and/or gear pumps.

In one implementation, the system 100 includes peristaltic pumps, and therefore is able to transfer wastewater samples through the various components of the system without exposing the mechanism of the peristaltic pumps to wastewater samples. More specifically, the first pump 120 can include a first peristaltic pump; and the second pump 140 can include a second peristaltic pump.

The inclusion of peristaltic pumps in the system 100 avoids potential corrosion of the pump mechanism, prevents any chemically reactive surfaces of the pump from interacting with the sample, and prevents accumulation of solid waste on pump components. Additionally, the inclusion of peristaltic pumps in the system 100 facilitates removal of the internal tubing of the system 100. For example, silicon tubing routed through a peristaltic pump in the system 100 can easily be removed with minimal disassembly of the peristaltic pump. Furthermore, a system 100 including peristaltic pump need not include valves (though they can be included to reduce the risk of backflow through particular components as a result of an error or accident) because peristaltic pumps occlude the tubing through the peristaltic pumps when not actively pumping.

The system 100 can include peristaltic pumps of different flow rates or pump heads. For example, the system 100 can include a first peristaltic pump with a first pump 120 head sufficient to draw water up from the sewage flow into the system and through the solid waste filter 132s and a second peristaltic pump with a second pump 140 head less than the first pump 120 head sufficient to draw water from the fluid repository 160, through the SPE cartridge 134, and out of the outlet port 114.

In one implementation, the system 100 includes flexible and chemically inert tubing (e.g. silicon tubing), which fluidly couples each of the fluidly coupled components of system 100. The system 100 can also include tube width adapters and rigid chemically inert ninety-degree bends, or other shaped components, to avoid kinking or the accidental occlusion of any flexible tubing used in the same context.

In one implementation, the system 100 includes electronically or hydraulically actuated valves that can switch the flow of wastewater through the system 100. For example, a two-way diverter valve can be fluidly coupled to the inlet of the fluid repository 160 allowing wastewater to flow into the fluid repository 160 from the outlet of the solid waste filter 132 or, alternatively, allowing wastewater to flow from the fluid repository 160 into the inlet of the SPE cartridge 134. Additionally or alternatively, the system 100 can include a multi-way diverter valve between a set of SPE cartridge 134s so that wastewater can be selectively routed to each SPE cartridge 134. However, the system 100 can include any number of flow control devices for controlling the flow of wastewater in the system 100.

6.5 Controller

Figure 4:
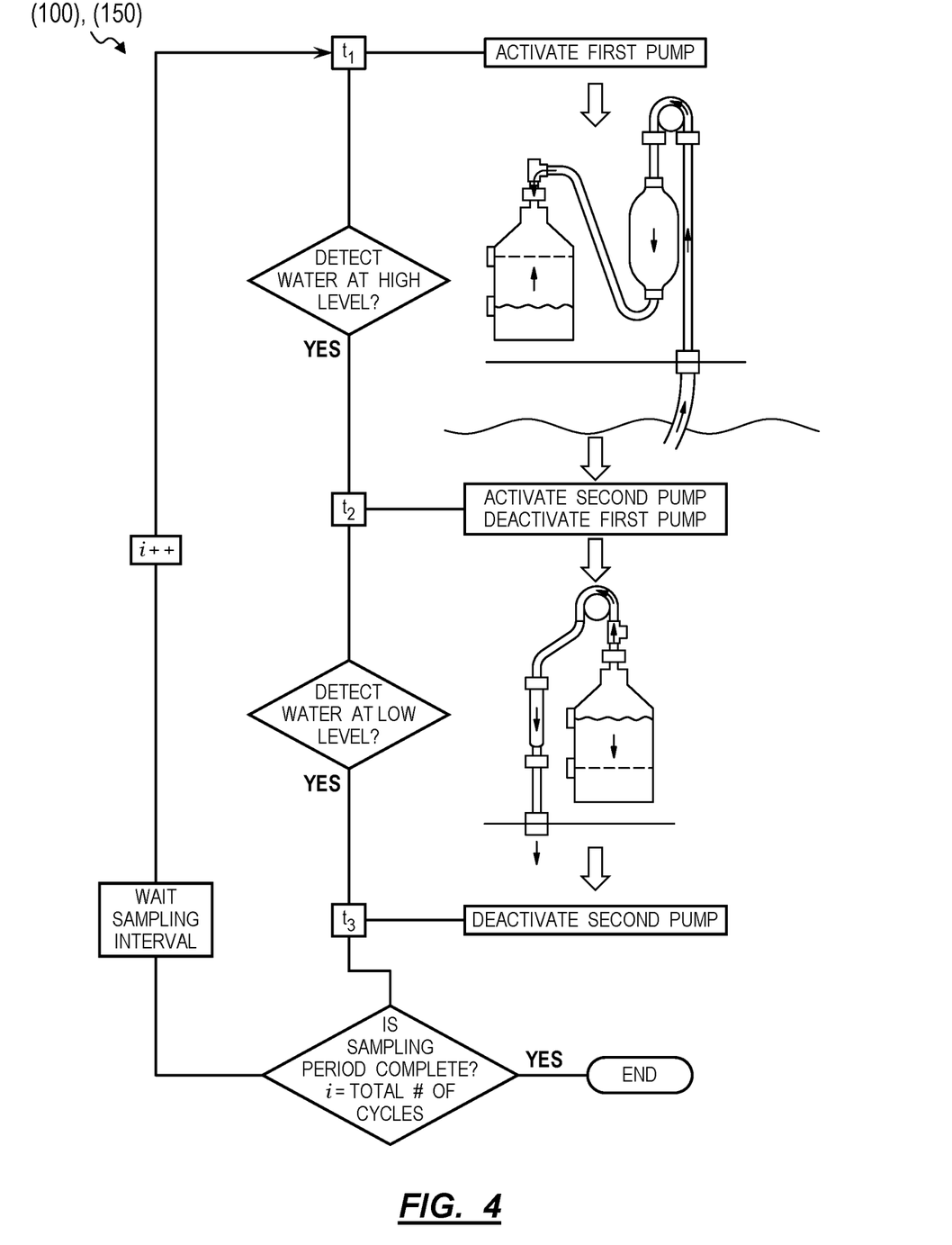
FIG. 4 is a flowchart representation of a second method

As shown in FIG. 4, in the variation of the system 100 including the fluid repository 160, the system 100 also includes a controller 150 that is configured to: activate the first pump 120 to draw wastewater through the inlet port, through the solid waste filter 132, and into the fluid repository 160 (i.e. the uptake cycle); responsive to detecting the presence of water at the high-level point via the high-level capacitive sensor, deactivate the first pump 120 and activate the second pump 140 to draw a filtered wastewater sample from the fluid repository 160, through the solid-phase extraction cartridge 134, and out of the outlet port 114 (i.e. the outlet cycle); and responsive to detecting the absence of water at the low-level point via the low-level capacitive sensor, deactivate the second pump 140. Generally, the controller 150 is a computational device that is either housed within the external casing of the system 100 or remote to the system 100, which controls the electronic functions of the system 100, especially the coordination of the pumps for sampling wastewater. For example, the system 100 can include a computer including a processor and memory configured to operate the first pump 120 and second pump and read capacitive signals from the low-level capacitive sensor and the high-level capacitive sensor. As such, the system 100 can include a controller 150 that is electrically coupled to the first and second pump 140s, the low-level and high-level capacitive sensors, and a power source (e.g. a battery or a 120-volt alternating current source). Alternatively, the system 100 can include a remote computational device acting as the controller 150. The remote controller 150 can communicate with a secondary processor housed within the external casing of the system 100, which can execute the instructions received from the remote controller 150 and transmit sensor readings and other information pertaining to control of the system 100.

In one implementation, the system 100 includes a controller 150 configured with a first threshold capacitance value associated with the low-level capacitive sensor indicating an absence of wastewater at the low-level point of the fluid repository 160 and a second threshold capacitance value associated with the high-level capacitive sensor indicating a presence of wastewater at the low-level point. In one implementation, the controller 150 can be used to calibrate the low-level and the high-level capacitive sensors to calculate the first and the second threshold capacitance values.

The system can include a controller 150 configured to initiate a sampling period at a sampling time after the system 100 has been deployed. Alternatively, the system 100 can include an electromagnetic antenna for wireless communication with a network such as the internet to determine when to initiate a sampling period. In another implementation, the system 100 includes a controller 150 configured to initiate multiple sampling periods, each of the sampling periods corresponding to a separate SPE cartridge 134 and/or solid waste filter 132. In yet another implementation, the system 100 can include a controller 150 configured to initiate sampling periods less than twenty-four hours in duration to obtain higher resolution wastewater data for particular times of day or for a particular event.

In one implementation, the system 100 includes a controller 150 configured to process a wastewater sample from the sewage flow at a sampling interval of one hour for the sampling period. In another implementation, the system 100 can include a controller 150 configured to increase the sampling rate proportional to an estimated flow rate of the sewage flow, wherein a sampling rate of once per hour corresponds to the estimated average flow rate of the sewage flow. In the implementation in which the sampling rate is proportional the estimated flow rate, the controller 150 can be preprogrammed with a sampling schedule based on historical flow patterns for the sewage flow. Alternatively, the system 100 can include a flowmeter capable of estimating the flow rate of the sewage flow electrically coupled to the controller 150, wherein the controller 150 is configured to adjust the sampling rate according to the estimated flow rate of the sewage flow. The system 100 can include a downward facing camera configured to obtain photographs of the sewage flow. The controller 150 can be configured to use machine vision algorithms to estimate the flow rate of the sewage flow and adjust the sampling rate of the system 100 accordingly.

The system 100 can include a controller 150 configured to, upon initiating the sampling process, time the duration of the uptake cycle to identify whether the duration of the uptake cycle has exceeded a threshold uptake time (e.g. fifteen minutes). Upon determining that the duration of the uptake cycle has exceeded the threshold uptake time, the controller 150 can be configured to cancel the sampling period and/or indicate to a user of the system that at least one uptake cycle in the sampling period failed to complete within the threshold time.

The system 100 can also include externally visible LEDs (e.g. located on the top of the external casing), electrically coupled to a controller 150 configured to operate the LEDs in response to various statuses of the system 100. For example, a separate color or blinking pattern of an LED can indicate: a sample has not yet been taken, a sampling period is in progress, a sampling period is complete, a sampling period has failed, the system 100 has low battery, or any other information that can be provided to the system. Alternatively, in implementations in which the system 100 is capable of wireless communication, more detailed status notifications can be sent via a short-range wireless protocol, such as Bluetooth.

However, the system 100 can include a controller 150 that is configured to operate the various electrically powered components of the system in any other way.

7. Replaceability and Service

The system 100 is designed to have easily replaceable and serviceable components. Generally, the inlet tube 112, the solid waste filter 132, the fluid repository 160, the SPE cartridge 134, and a battery can all be removed from the system and replaced when necessary for analysis or service. Additionally, any of the tubing fluidly coupling each of the aforementioned components to each other can also be removable and replaceable. In one implementation, each component can be removed and replaced separately using standard detachment and attachment methods such as threaded interfaces, snaps, latches, magnets, etc.

Alternatively, the system 100 can include a replaceable cartridge that is configured to include multiple components. For example, the replaceable cartridge can include the solid waste filter 132, the fluid repository 160, and the SPE cartridge 134, such that the replaceable cartridge and all of the aforementioned components can be removed in a single step.

8. Fluid Circuit Variation

As shown in FIGS. 1A and 1B, one variation of the system 100 includes two fluid circuits including a high-flow circuit 110 and a sampling circuit 130. The high-flow circuit 110 connects the inlet tube 112 with an outlet port 114 (e.g., a high-flow outlet port 114) and includes a first pump 120 configured to pump wastewater from the sewage flow, through the inlet tube 112, and back out of the outlet port 114. Therefore, the high-flow circuit 110 functions to draw a steady supply of wastewater from the sewage flow into the system 100 to enable the system 100 to divert precise volumes of wastewater from the high-flow circuit 110 via the sampling circuit 130 for sampling by activating a second pump 140. Thus, by including two separate circuits (one for obtaining wastewater from the sewage flow and another for sampling), this variation of the system is able to separate the functions of the two pumps and therefore include pumps configured for the respective functions. The system 100 can therefore include a first pump 120 (in line with the high-flow circuit 110) with a high flow rate and low flow accuracy and a second pump 140 (in line with the sampling circuit 130)

with a low flow rate but a high degree of flow accuracy. This variation is further described below.

8.1 High-Flow Outlet Port

In the variation of the system 100 including a high-flow circuit 110 and a sampling circuit 130, the system 100 can include a high flow outlet port 114 for the high-flow circuit 110. The system 100 can include a high-flow outlet port 114 coupled to and traversing an outer shell of the external casing, such that wastewater from the high-flow circuit 110 can flow back out of the system 100 into the sewage flow. The system 100 includes the high-flow outlet port 114 such that the first pump 120 is able to continuously pump wastewater through the high-flow circuit 110 for sampling by the sampling circuit 130.

8.1.1 Flow Restrictor

In one implementation, the system 100 can include a flow restrictor coupled to the high-flow outlet port 114 in order to maintain backpressure in the high-flow circuit 110 and to enable more consistent sampling from the high-flow circuit 110 into the sampling circuit 130. More specifically, the system 100 can include a flow restrictor coupled to the outlet port 114 and configured to maintain a backpressure in the high-flow circuit 110 sufficient to enable consistent flow of wastewater from the high-flow circuit 110 into the sampling circuit 130 during activation of the second pump 140. The system can include any type of flow restricting valve or opening configured to provide consistent flow into the high-flow circuit 110.

8.2 High-Flow Circuit

As shown in FIGS. 1A and 1B, the system 100 can include a high-flow circuit 110 (e.g., a fluid circuit) fluidly coupling the inlet tube 112 to an outlet port 114 (e.g., the high-flow outlet port 114) and engaging with a first pump 120 (e.g., a high-flow pump). Generally, the high-flow circuit 110 can include flexible and chemically inert tubing and/or any rigid pieces to direct the flow of wastewater from the sewage flow, into the system 100 and back out of the outlet port 114. As briefly discussed above, the high-flow circuit 110 is configured to pump a sufficient flow rate of wastewater into the system such that the system can divert a portion of that wastewater into the sampling circuit 130 in order to deposit drug metabolites in the SPE cartridge 134 and bacteria samples in the solid waste filter 132 included therein.

The flexible tubing of the high-flow circuit 110 engages with the first pump 120 (e.g., the high-flow pump). In implementations wherein the first pump 120 is a peristaltic pump, the flexible tubing of the high-flow circuit 110 can be configured to engage with an open channel of the first peristaltic pump during installation, thereby enabling the first peristaltic pump to utilize the tubing of the high-flow circuit 110 itself as the occluded tubing for the peristaltic pump. Thus, the tubing of the high-flow circuit 110 can define an inner diameter, outer diameter, and a wall thickness configured to engage with the first peristaltic pump. In order to provide a higher flow rate in the high-flow circuit 110, the system 100 can include a high-flow circuit 110 defining a larger inner diameter, thereby increasing the cross-sectional area of the high-flow circuit 110 and increasing the maximum flow rate of the first peristaltic pump.

8.2.1 Junction

As shown in FIGS. 1A and 1B, the high-flow circuit 110 can include a junction 116 fluidly coupling the high-flow circuit 110 to the sampling circuit 130 and enabling the sampling circuit 130 to divert wastewater from the high-flow circuit 110 to the sampling circuit 130. The system 100 can include any type of junction 116 such as a T-junction 116, Y-junction 116, diverter valve, or any other junction 116 configured to initiate one fluid channel from another fluid channel. In implementations of the system 100 including peristaltic pumps, the system 100 can include open junctions (e.g., junctions not controlled by a valve) because the backpressure applied via occlusion of the sampling circuit 130 by the second peristaltic flow prevents wastewater from diverting from the high-flow circuit 110 into the sampling circuit 130 unless the peristaltic pump (e.g., second pump 140) of the sampling circuit 130 is activated.

However, the system 100 can include a junction 116 of any type capable of fluidly coupling the high-flow circuit 110 to the sampling circuit 130.

8.3 High-Flow Pump

As shown in FIGS. 1A and 1B, the system 100 can include a first pump 120 or a high-flow pump configured to pump wastewater from the sewage flow via the inlet tube 112, through the high-flow circuit 110, and out of the outlet port 114. Generally, the system 100 can include various types of pumps such as peristaltic pumps, diaphragm pumps, and/or gear pumps. In one implementation, the system 100 includes a peristaltic pump as the high-flow pump, and therefore is able to transfer wastewater samples through the various components of the system without exposing the mechanism of the peristaltic pumps to wastewater samples. More specifically, the first pump 120 can include a first peristaltic pump.

8.4 Sampling Circuit

As shown in FIGS. 1A and 1B, in this variation, the system 100 includes a sampling circuit 130, which functions to collect bacterial and drug metabolite samples from wastewater flowing through the sampling circuit 130. Generally, the sampling circuit 130 includes flexible plastic tubing fluidly coupled in series to the solid waste filter 132 and the SPE cartridge 134 in that order. As described above with respect to the high-flow circuit 110, the tubing of the sampling circuit 130 can also define an inner diameter, outer diameter, and wall thickness configured to engage with a peristaltic pump (e.g., the second peristaltic pump). In one implementation, the system 100 includes a sampling circuit 130 that terminates in a second outlet port 114 (i.e. a sampling outlet port 114) such that once the system has processed wastewater via the solid waste filter 132 and the SPE cartridge 134, the sampled water can be discarded via an outlet port 114. In an alternative implementation, the system 100 can include a sampling circuit 130 that terminates in a fluid repository 160 for later laboratory analysis (e.g., as a B-sample or as a sample volume measurement) upon collection of the solid waste filter 132 and the SPE cartridge 134. Individual components of the sampling circuit 130 are further described below.

8.4.1 Solid Waste Filter

In this variation including a sampling circuit 130, the system 100 includes a solid waste filter 132 configured to filter solid biological waste from the wastewater sample as it flows into the system 100 and before the wastewater sample flows through the SPE cartridge 134. Generally, the solid waste filter 132 removes bacteria and other large debris from the wastewater sample in order to prevent bacteria in the wastewater sample from contaminating the SPE cartridge 134 and degrading the wastewater sample therein. An inlet of the solid waste filter 132 is fluidly coupled to the junction 116 (and or an in-line peristaltic pump).

In one implementation, the system 100 includes a solid waste filter 132 with a pore size of less than 0.5 microns (i.e. sufficiently small to remove bacterial from the wastewater sample). Additionally, the system 100 can include a solid waste filter 132 that has a chemically inert filtering medium, so as not to affect the chemistry of the wastewater sample.

In one implementation, the system 100 includes a solid waste filter 132 that is replaceable and configured to be disconnected from the surrounding internal tubing by a user interfacing with the system 100. In one implementation, the filtering medium can be removed from the housing of the solid waste filter 132 for testing, cleaning and sterilization, or replacement. Additionally, the contents of the solid waste filter 132 can be tested by users of the system 100. Therefore, the system 100 can include a solid waste filter 132 that is compatible with 16S rDNA sequencing, micro-biological culture, or any other bacterial or viral profiling test. In one implementation, the system 100 can include multiple successive solid waste filters 132 of increasingly small pore size to better separate solid waste from free floating bacteria and/or viruses. The system 100 can include a viral filter as part of a secondary solid waste filter 132, wherein the viral filter has a pore size of less than 0.1 microns. Thus, the system 100 can include a pore size configured to capture bacteria and/or viruses from wastewater.

However, the system 100 can remove bacteria and other solid waste from the sample in any other way.

8.4.2 SPE Cartridge

In the variation of the system including the sampling circuit 130, the system 100 includes an SPE cartridge 134 configured to extract dissolved drug metabolites from water. Generally, the SPE cartridge 134 provides a means for extracting drug metabolites, other drug associated chemicals, or any other chemicals present in the wastewater sample for later analysis via mass spectrometry of the extracted chemicals from the SPE cartridge 134, upon removal of the SPE cartridge 134 from the system 100. Thus, the system 100 includes a removable and replicable SPE cartridge 134. The system 100 includes the SPE cartridge 134 with an inlet fluidly coupled to the outlet of the solid waste filter 132 and an outlet fluidly coupled to the sampling outlet port 114 of the external casing and the overall system 100 or to a fluid repository 160 for B-sample storage as is further described above. Therefore, after pumping the wastewater through the SPE cartridge 134, the system can route the wastewater sample through an outlet port 114 of the external casing to discard the sample.

In one implementation, the system 100 includes an SPE cartridge 134 with a stationary phase having analytes configured to bind with target functional groups of particular drug metabolites or other target chemicals that may be present in the wastewater sample. Therefore, the system can include an SPE cartridge 134 configured to extract drug metabolites from wastewater while sewage flows through the SPE cartridge 134. However, the system 100 can extract drug metabolites or other target chemicals from the wastewater sample in any other way.

In another implementation, the system 100 includes an SPE cartridge 134 defining a sample volume specification indicating a particular volume of wastewater that can be processed by the SPE cartridge 134 prior to saturation of the stationary phase of the SPE cartridge 134 with various analytes from the wastewater. Thus, the system 100 includes a controller 150 and pump hardware configured to direct approximately the sample volume specification of the SPE cartridge 134 through the sampling circuit 130 for each individual sample.

In yet another implementation, the system 100 includes a set of multiple SPE cartridge 134s and each SPE cartridge 134 is included in its own sampling circuit 130 in the system 100. For example, each SPE cartridge 134 in the set can be individually fluidly coupled to the junction 116 of the high-flow circuit 110 (e.g. via multiple tube junction 116s or diverter valves) and to the outlet port 114. Furthermore, each SPE cartridge 134 can include an associated pump (further described below) to move wastewater samples through each SPE cartridge 134. Alternatively, the system 100 can include a single pump coupled to a diverter valve to selectively pump water through each of the set of SPE cartridge 134s. More specifically, the system 100 can include a sampling circuit 130 including: a diverter valve fluidly coupled to the outlet of the solid waste filter 132 and defining a set of outlets; a set of solid-phase extraction cartridges 134, each solid-phase extraction cartridge 134 in the set of solid-phase extraction cartridges 134 fluidly coupled to an outlet in the set of outlets defined by the diverter valve; and a controller 150 configured to: during a first sampling cycle, activate the first pump 120 to direct wastewater flow to a first SPE cartridge 134; and during a second sampling cycle, actuate the diverter valve to direct flow of wastewater to a second solid-phase extraction cartridge 134 in the set of solid-phase extraction cartridges 134. Thus, the system 100 can be capable of performing multiple sampling periods before being serviced or replaced.

8.5 Sampling Outlet Port

In one implementation, the system 100 includes a second outlet port 114 (i.e. a sampling outlet port 114) that functions as an outlet for wastewater from the sampling circuit 130. Similar to the high-flow outlet port 114, the sampling outlet port 114 can include a flow restrictor to provide backpressure to the sampling circuit 130.

8.6 Sampling Pump

As shown in FIGS. 1A and 1B, the system 100 includes a sampling pump (i.e. the second pump 140) in-line on the sampling circuit 130. Generally, the system 100 can include a sampling pump such as a peristaltic pump, diaphragm pump, and/or a gear pump. More specifically, the system 100 can include a sampling pump arranged along the sampling circuit 130 before the solid waste filter 132 in order to pump wastewater into the solid waste filter 132 and successively into the SPE cartridge 134. Alternatively, the system 100 can include a sampling pump arranged in another location along the sampling circuit 130 in order to pump wastewater through the sampling circuit 130.

In variations of the system 100 including a sampling circuit 130, the sampling pump is configured to precisely dose volumes of wastewater for filtering by the SPE cartridge 134. Additionally, the sampling pump can operate at a lower flow rate such that analytes may bind to the SPE filter and in order to prevent rinsing sample analytes from the sample. Therefore, the system 100 can include a sampling pump capable of maintaining a stable flow rate at as low as five milliliters per minute and as high as 50 milliliters per minute.

8.7 In-Line Flowmeter

In one implementation, the system 100 can include an in-line flowmeter to determine the volumetric flow rate of wastewater in the sampling circuit 130. Generally, the in-line flowmeter functions to provide a measurement of the flow rate through the sampling circuit 130 such that the system can control the volume of wastewater flowing through the SPE filter and ensure that each sampling cycle in the sampling period achieves an intended sampling volume. In particular, the system 100 can execute closed loop controls via the in-line flowmeter and the second pump 140 in order to control the volume of wastewater in each sampling cycle. Therefore, the system 100 can include a flowmeter fluidly coupled in-line on the sampling circuit 130 and configured to measure a flow rate through the sampling circuit 130.

Depending on the implementation, the in-line flowmeter can include mechanical flowmeters, pressure-based flowmeters, optical flowmeters, and/or ultrasonic flowmeters. Additionally, the in-line flowmeter can be arranged at any point along the sampling circuit 130.

8.8 Controller

Figure 3:
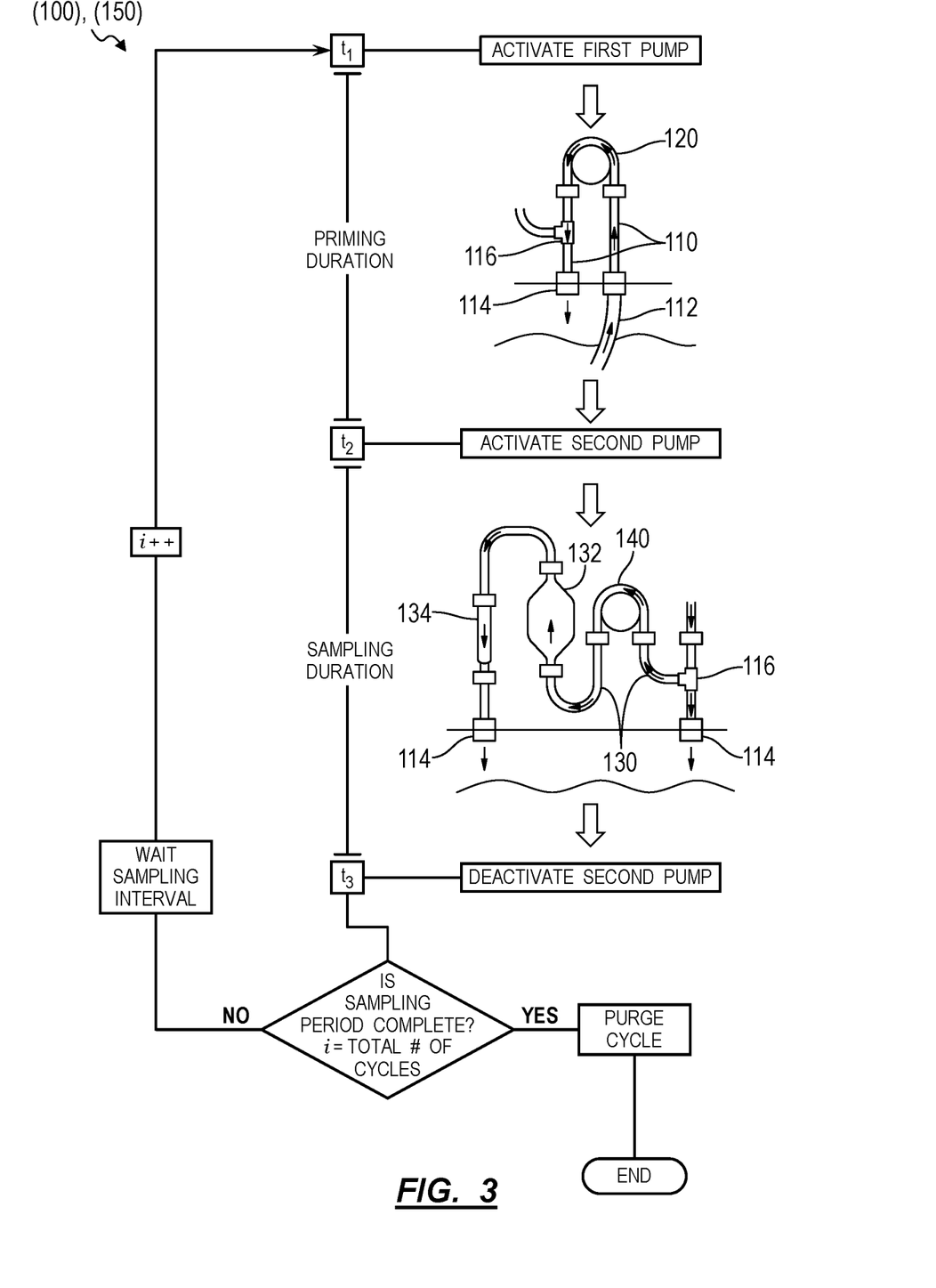
FIG. 3 is a flowchart representation of a first method.

As shown in FIG. 3 and in variations of the system 100 including a high-flow circuit 110 and a sampling circuit 130, the controller 150 can activate the first pump 120 and the second pump 140 of the system in order to execute a series of sampling cycles over a sampling period. In some implementations, the system 100 can include a controller 150 configured to: adjust the flow rate and/or the flow direction of the first pump 120 and the second pump 140 in order to precisely control the volume of wastewater passing through the solid waste filter 132 and the SPE cartridge 134; prime the circuit for a sampling cycle; and/or purge the system of wastewater prior to collection of the wastewater sample. Furthermore, the system 100 can include a controller 150 capable of executing sampling cycles according to a variable volume sampling schedule over a sampling period. The functions of the controller 150 are further described below.

8.8.1 Sampling Cycle

The system 100 includes a controller 150 configured to execute a sampling cycle in order to: draw a continuous stream of wastewater from the sewage flow into the system 100 by activating the first pump 120 on the high-flow circuit 110; divert a portion of the wastewater from the high-flow circuit 110 into the sampling circuit 130; control the flow rate in the sampling circuit 130 via the second pump 140; and, succeeding a sampling duration, deactivate the second pump 140 to cease the flow of wastewater through the SPE filter.

Thus, the system 100 can include a controller 150 configured to execute several phases in each sampling cycle. In an uptake phase (e.g., at a first time), the controller 150 can activate the first pump 120 in order to draw wastewater from the sewage via the inlet tube 112, through the high-flow circuit 110, and out of the outlet port 114. In a sampling phase (e.g., at a second time succeeding the first time), the controller 150 can also activate the second pump 140 in order to divert wastewater from the high-flow circuit 110 for a sampling duration. After the second pump 140 has been active for the sampling duration, the controller 150 can deactivate the second pump 140 (e.g., at a third time succeeding the second time by a sampling duration). In some implementations, the uptake phase (e.g., between the first and the second time) can last for a priming duration in order to rinse wastewater from a previous sampling from the high-flow circuit 110. Therefore, the system can include a controller 150 configured to, during a sampling cycle and at a second time succeeding the first time by a priming duration, activate the second pump 140 to divert wastewater from the high-flow circuit 110 into the sampling circuit 130 via the junction 116.

In one implementation, the system 100 includes a controller 150 configured to execute a sampling cycle with a sampling duration of twenty seconds. Although, the system 100 can divert wastewater into the sampling circuit 130 for a consistent amount of time between sampling cycles, the controller 150 can vary the flow rate of the second pump 140 thereby also varying the sampling volume of each sampling cycle. Therefore, the system 100 can include a controller 150 configured to adjust the sampling volume of each sampling cycle proportional to the flow rate (or approximate flow rate) of the sewage flow at the time of the sampling cycle.

8.8.2 Sampling Schedule

The system 100 can include a controller 150 configured to execute sampling cycles according to a sampling schedule over a sampling period. More specifically, the system 100 can include a controller 150 configured to periodically execute a series of sampling cycles over a daily sampling period. In particular, the system 100 can include a controller 150 that schedules sampling cycles at sufficiently short intervals to capture individual (toilet) flushing events in the sewage flow while still being long enough to account for the maximum volume specification of the SPE cartridge 134 (e.g., too many sampling cycles can result in greater than the maximum volume specification of wastewater flowing through the SPE cartridge 134). Thus, by scheduling sampling cycles according to the sampling schedule, the system 100 can ensure that the analyte samples collected in the solid waste filter 132 and the SPE cartridge 134 are more representative of the total mass of the analyte present in the sewage flow over the entire sampling period.

In one implementation, the system 100 includes a controller 150 configured to schedule sampling cycles according to a fluid flow model. In this implementation, the sampling interval of the sampling schedule can be calculated according to the duration of a flush in the sewage flow. The fluid flow model can take into account a sewage map and the level of molecular dispersion and can simulate the average (or another central measurement statistic) duration of a flush at a planned location of the system 100 in the sewer system. The system 100 can, therefore, include a controller 150 configured to schedule sampling cycles with a sampling interval less than the duration of a flush in the sewer system (or a specified number of standard deviations lower than the duration of a flush depending on a desired accuracy of the system). More specifically, the system 100 can include a controller 150 configured to periodically execute the series of sampling cycles separated by a sampling interval consistent with a fluid flow model defining a flush duration in the sewage flow.

In implementations of the system 100 wherein the flowrate of the second pump 140 is not controllable by the system 100 (e.g., the second pump 140 operates at a single flow rate), the controller 150 can be configured with a sampling schedule that indicates variable length sampling durations for each sampling cycle proportional to a predicted (or measured) flow rate of the sewage flow at the time of each sampling cycle. Therefore, the system 100 can ensure that the total volume of the wastewater passing through the sampling circuit 130 during a sampling period is proportionally representative of the sewage flow during the sampling period.

8.8.3 Flow Rate Control

In implementations of the system 100 including a second pump 140 with a variable (i.e. controllable) flow rate, the system 100 can include a controller 150 configured with a sampling schedule specifying a target flow rate corresponding to each sampling cycle in a sampling period. Therefore, although each sampling cycle in the sampling period can be characterized by the same sampling duration, the volume of wastewater passing through the sampling circuit 130 during the sampling cycle can vary approximately proportional to the predicted (or measured) flowrate in the sewage flow at the location of the system 100. Therefore, the system 100 can ensure an analyte sample in the SPE cartridge 134 that is approximately representative of the total mass of analyte in the sewage flow. More specifically, the system 100 can include a controller 150 configured to, for each sampling cycle in the series of sampling cycles, access a target flow rate of the second pump 140 proportional to an approximate flow rate of the sewage flow during the sampling cycle, wherein a total volume of wastewater passing through the solid-phase extraction cartridge 134 over the sampling period is approximately equal to a sample volume specification of the solid-phase-extraction cartridge 134.

In one implementation, the system 100 can include a controller 150 configured to vary the target flow rate of a sampling cycle according to a current measured or estimated flowrate of the sewage flow. Thus, the system 100 can adjust the target flow rate for the second pump 140 in real-time in response to changes in the flow rate of the sewage flow.

In another implementation, the system 100 can include a controller 150 configured to execute closed-loop control of the second pump 140 to ensure that the second pump 140 is diverting an accurate flow rate of wastewater through the sampling circuit 130. Therefore, the system 100 can include a flow meter arranged along the sampling circuit 130 and configured to measure the flow rate of wastewater through the sampling circuit 130. Therefore, the system 100 can include a flowmeter fluidly coupled in-line on the sampling circuit 130 and configured to measure a flow rate through the sampling circuit 130; and a controller 150 configured to, during the sampling cycle and during activation of the second pump 140, measure the flow rate of wastewater through the sampling circuit 130; and execute closed-loop control of the second pump 140 to achieve a target flow rate of wastewater through the sampling circuit 130.

8.8.4 Purge Cycle

In one implementation, the system 100 can include a controller 150 configured to purge wastewater from the system prior to collection of samples from the system 100 in order to prevent leakage of wastewater from the system 100 during transportation of the sample. More specifically, the system 100 can include a controller 150 configured to activate the first pump 120 and the second pump 140 of the system according to a purge cycle to remove wastewater from the system. In particular the system 100 can include a controller 150 configured to, during a purge cycle subsequent to the daily sampling period: activate the first pump 120 in reverse to initiate air flow through the high-flow circuit 110 and remove excess wastewater from the high-flow circuit 110; and activate the second pump 140 to initiate air flow from the high-flow circuit 110 through the sampling circuit 130 via the junction 116 and remove excess wastewater from the sampling circuit 130. Thus, the system 100 can force any remaining wastewater in the system out of one or more outlet port 114s of the system.

8.9 Replaceable Filter Kit

In one variation of the system 100, shown in FIG. 1B, the system 100 includes at least two components: a sampling assembly 102 including the inlet tube 112, the first pump 120, the outlet port 114, the second pump 140, and the controller 15o; and a replaceable filter kit 104 including the high-flow circuit 110 and the sampling circuit 13o. Thus, when retrieving samples from the system 100 or performing maintenance on the system 100, a user can simply remove the replaceable filter kit 104 and, at once, remove all components of the system that most frequently require replacement or collection (e.g., of a sample). The system 100 can include a set of replaceable filter kit 104s such that, upon collection of a sample via removal of a first sample kit, a user can insert a second replaceable filter kit 104 into the sampling assembly 102.

In this implementation, the system 100 includes peristaltic pumps that can open and close to accept new tubing of the high-flow circuit 110 and sampling circuit 130 in each replaceable filter kit 104 in order to enable quick and easy removal or installation of the replaceable filter kit 104. Furthermore, the system 100 can include a replaceable filter kit 104 and a sampling assembly 102 mutually configured to fit together and detach via any type or types of attachment mechanism such as clips, latches, hook-and-loop attachment, etc.

In one implementation, the system 100 includes a refresh plate or other mechanical element that provides structural stability to each of the components included in the replaceable filter kit 104 and locates them within the sampling assembly 102 upon installation of the replaceable filter kit 104 within the sampling assembly 102.

8.9.1 Quick Disconnect Fittings

In implementations of the system 100 including a sampling assembly 102 and a replaceable filter kit 104, the system can also include a set of quick disconnect fittings in order to prevent leakage of wastewater onto users removing a replaceable filter kit 104 from a sampling assembly 102. More specifically, the system 100 can include: a first quick disconnect fitting arranged at an interface between the inlet tube 112 and the high-flow circuit 110 and configured to seal excess wastewater within the high-flow circuit 110 upon removal of the replaceable filter kit 104; a second quick disconnect fitting arranged at an interface between the first outlet port 114 and the high-flow circuit 110 and configured to seal excess wastewater within the high-flow circuit 110 upon removal of the replaceable filter kit 104; and a third quick disconnect fitting arranged at an interface between the second outlet port 114 and the sampling circuit 130 and configured to seal excess wastewater within the sampling circuit 130 upon removal of the replaceable filter kit 104.

The set of quick disconnect fittings can include any type of quick disconnect fitting. Additionally, the male and/or female end of the quick disconnect fitting can be coupled to either the sampling assembly 102 or the replaceable filter kit 104 depending on the implementation. In another implementation, the system can also include self-sealing values arranged at an open end of each quick disconnect fitting in order to further prevent any leakage of wastewater from the replaceable filter kit 104 upon removal of the replaceable filter kit 104 from the sampling assembly 102.

8.9.2 Replacement Prompts

In implementations of the system 100 including a sampling assembly 102 and a replaceable filter kit 104, the system 100 can also include a controller 150 configured to prompt users of the system to collect the replaceable filter kit 104 in order to prevent analyte samples from degrading with the SPE cartridge 134 or the solid waste filter 132 between initial sampling and collection by a user of the system 100. Therefore, the system 100 can periodically execute a series of sampling cycles over a sampling period; and, succeeding the sampling period, prompt a user to replace the replaceable filter kit 104.

In one implementation, the system 100 can include an LED indicator arranged on the external casing proximal a top of the external casing and can include a controller 150 configured to change the color or turn on the LED in response to completion of a sampling period such that a user of the system 100 can view the LED and ascertain the state of the system. In an alternative implementation, the system 100 can include a wireless transmitter and a controller 150 configured to transmit a prompt indicating completion of a sampling period in response to completing a sampling period.

However, the system 100 can include any other means for generating a prompt or otherwise alerting a user of the system 100 that a sample is ready for collection.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:
1. A wastewater sampling system comprising:
an inlet tube extending into a sewage flow;
a first pump configured to pump wastewater from the sewage flow into the wastewater sampling system;
a solid waste filter fluidly coupled to the inlet tube;
a fluid repository fluidly coupled to an outlet of the solid waste filter;
the first pump is further configured to draw wastewater through the inlet tube, through the solid waste filter, and into a fluid repository;
a solid-phase extraction cartridge fluidly coupled to an outlet the fluid repository;
a second pump configured to pump volumes of wastewater from the fluid repository through the solid phase extraction cartridge to an outlet port; and
a controller configured to:
periodically execute a series of sampling cycles over a sampling period;
for each sampling cycle in the series of sampling cycles, access a target flow rate of the second pump proportional to an approximate flow rate of the sewage flow during the each sampling cycle; and
during each sampling cycle in the series of sampling cycles:
at a first time, activate the first pump to initiate sewage flow into the wastewater sampling system through the inlet tube, through the solid waste filter, and into the fluid repository;
at a second time succeeding the first time, activate the second pump to pass wastewater from the fluid repository to the solid-phase extraction cartridge at the target flow rate; and
at a third time succeeding the second time by a sampling duration, deactivate the second pump.

* * * * *

UNITED STATES PATENT AND TRADEMARK OFFICE
CERTIFICATE OF CORRECTION

PATENT NO. : 11,714,030 B2
APPLICATION NO. : 16/528465
DATED : August 1, 2023
INVENTOR(S) : Mariana G. Matus Garcia et al.

It is certified that error appears in the above-identified patent and that said Letters Patent is hereby corrected as shown below:

In the Claims

In Column 24, Line(s) 13, Claim 1, after "outlet", insert --of--.

Signed and Sealed this
Seventeenth Day of October, 2023

*Katherine Kelly Vidal*

Katherine Kelly Vidal
*Director of the United States Patent and Trademark Office*